United States Patent
Li et al.

(10) Patent No.: US 10,590,154 B2
(45) Date of Patent: Mar. 17, 2020

(54) METHOD FOR PREPARING OXAZOLIDINONE INTERMEDIATE

(71) Applicants: Zhejiang Huahai Pharmaceuticals Co., Ltd, Linhai (CN); Shanghai Aobo Pharmtech, Inc., Ltd., Shanghai (CN)

(72) Inventors: Siyuan Li, Shanghai (CN); Shaoxiao Gui, Shanghai (CN); Genliang Wang, Shanghai (CN); Jicheng Zhang, Shanghai (CN); Luning Huang, Shanghai (CN); Anping Tao, Shanghai (CN); Hong Gu, Shanghai (CN)

(73) Assignees: ZHEJIANG HUAHAI PHARMACEUTICAL CO., LTD, Linhai (CN); SHANGHAI AOBO PHARMTECH, INC., LTD., Shanghai (CN)

( * ) Notice: Subject to any disclaimer, the term of this patent is extended or adjusted under 35 U.S.C. 154(b) by 0 days.

(21) Appl. No.: 15/771,449

(22) PCT Filed: Nov. 2, 2016

(86) PCT No.: PCT/CN2016/104360
§ 371 (c)(1),
(2) Date: Apr. 27, 2018

(87) PCT Pub. No.: WO2017/076293
PCT Pub. Date: May 11, 2017

(65) Prior Publication Data
US 2018/0312476 A1   Nov. 1, 2018

(30) Foreign Application Priority Data
Nov. 3, 2015 (CN) ................. 2015 1 0739910

(51) Int. Cl.
*C07D 401/04* (2006.01)
*C07D 263/24* (2006.01)
(Continued)

(52) U.S. Cl.
CPC ......... *C07F 9/65583* (2013.01); *B01J 27/055* (2013.01); *B01J 27/122* (2013.01); *B01J 31/0212* (2013.01); *B01J 31/0238* (2013.01); *B01J 31/2295* (2013.01); *B01J 31/28* (2013.01); *B01J 31/30* (2013.01); *C07C 213/00* (2013.01); *C07C 217/40* (2013.01); *C07C 217/48* (2013.01); *C07C 231/10* (2013.01); *C07C 235/78* (2013.01); *C07D 263/20* (2013.01); *C07D 263/24* (2013.01); *C07D 401/04* (2013.01); *C07D 413/14* (2013.01); *B01J 2231/44* (2013.01); *B01J 2531/824* (2013.01)

(58) Field of Classification Search
CPC ................. C07D 263/20; C07D 263/24
See application file for complete search history.

(56) References Cited

U.S. PATENT DOCUMENTS

2008/0009465 A1  1/2008  Ryono et al.
2014/0206677 A1  7/2014  Basarab et al.

OTHER PUBLICATIONS

Danielmeier et al., "Efficient pathways to (R)- and (S)-5-hydroxymethyl-2-oxazolidinone and some derivatives", *Tetrahedron: Asymmetry*, 6(5):1181-1190, (1995).

(Continued)

*Primary Examiner* — Shawquia Jackson
(74) *Attorney, Agent, or Firm* — Norton Rose Fulbright US LLP

(57) ABSTRACT

The invention relates to a method for preparing an oxazolidinone intermediate. Specifically, a synthesis procedure for the intermediate comprises: directly performing a "one-pot" reaction on a compound I, compound J or compound L without performing isolation, wherein a salt of a compound K is selected from a hydrochloride, sulfate, malate, tartrate, p-toluenesulfonate, or lactate, and wherein the symbol * in a compound indicates an atom of an R-type chirality or an S-type chirality or a racemate thereof.

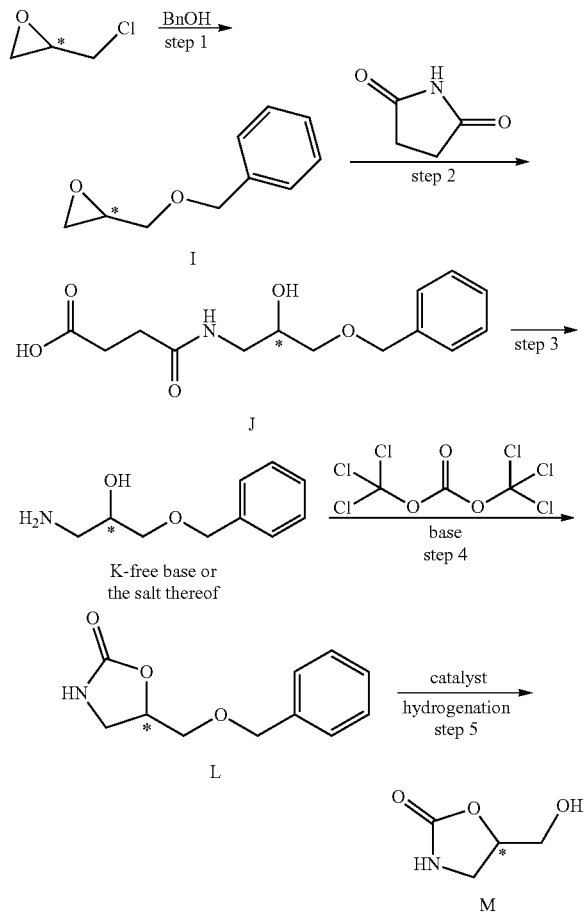

14 Claims, No Drawings

(51) Int. Cl.

| | | |
|---|---|---|
| *C07F 9/6558* | (2006.01) | |
| *C07D 413/14* | (2006.01) | |
| *C07C 213/00* | (2006.01) | |
| *C07C 217/48* | (2006.01) | |
| *C07C 231/10* | (2006.01) | |
| *C07C 235/78* | (2006.01) | |
| *C07D 263/20* | (2006.01) | |
| *C07C 217/40* | (2006.01) | |
| *B01J 27/055* | (2006.01) | |
| *B01J 27/122* | (2006.01) | |
| *B01J 31/02* | (2006.01) | |
| *B01J 31/22* | (2006.01) | |
| *B01J 31/28* | (2006.01) | |
| *B01J 31/30* | (2006.01) | |

(56) References Cited

OTHER PUBLICATIONS

Hamaguchi et al., "Enzymatic Resolution of 2-Oxazolidinone Esters", *Agricultural and Biological Chemistry*, 49(5):1509-1512, (1985).

International Search Report and Written Opinion issued in International Patent Application No. PCT/CN2016/104360, dated Feb. 9, 2017.

Kamal et al., "New Chemoenzymatic Pathway for β-adrenergic Blocking Agents," *Tetrahedron Asymmetry*, 16(8): 1485-1494, (2005).

Pischel et al., "Hydrophilic 1-(Carboxymethyl)-5-Fluorouracil Amides: Preparation and Cytostatic Activity" *Collection of Czechoslovak Chemical Communications*, 52(8):2061-9, (1987).

Pischel et al., "Hydrophilic 1-(Carboxymethyl)-5-Fluorouracil Amides: Preparation and Cytostatic Activity" *Collection of Czechoslovak Chemical Communications*, 52(8):2061-9, (1987) (Abstract Only).

Viti et al., "New Antagonists of Platelet-Activating Factor Containing 2-Oxazolidinone or 2-Morpholinone," *European Journal of Medicinal Chemistry*, 29(5):401-406, (1994).

Zhang et al., "Recent Advances in Syntheses of Oxazole Compounds,"*Chinese Journal of Organic Chemistry*, 31(12):1963-1976, (2011). (English Abstract).

Pallavicini et al., "Resolution of 5-hydroxymethyl-2-oxazolidinone by preferential crystallization and investigations on the nature of the racemates of some 2-oxazolidinone derivatives" *Tetrahedron: Asymmetry*, 2004, 15(10):1659-1665.

Partial Search Report issued in Corresponding European Patent Application No. 16861561, dated Apr. 23, 2019.

Sugimoto et al., "Synthesis and structure-activity relationship of a novel class of 15-membered macrolide antibiotics known as '11a-azalides'" *Bioorg. Med. Chem.*, 2012, 20(19):5787-5801.

METHOD FOR PREPARING OXAZOLIDINONE INTERMEDIATE

CROSS-REFERENCE TO RELATED APPLICATIONS

The present application is a national phase under 35 U.S.C. § 371 of International Application No. PCT/CN2016/104360, filed Nov. 2, 2016, which claims the priority of Chinese patent application No. 201510739910.6, with the title of "Method for Preparing Tedizolid and Intermediate thereof", filed on Nov. 3, 2015 The contents of each of the referenced applications are incorporated herein by reference.

FIELD OF THE INVENTION

The invention relates to a method for preparing an oxazolidinone intermediate.

BACKGROUND OF THE INVENTION

A new class of oxazolidinone antibacterial drugs is a new class of fully synthetic antibiotics that gradually developed in the 1980s, for example, linezolid and tedizolid. Such drugs have oxazolidinone as a mother nucleus in their chemical structures, and present a totally new antibacterial mechanism. They have relatively strong antibacterial activity against grain-positive cocci, especially multidrug-resistant grain-positive cocci, without cross-resistance with other drugs. Oxazolidinone is an important constituent fragment of this class of drug molecules, as shown below.

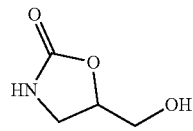

In the prior art, oxazolidinone can be obtained by ring closing of diethyl carbonate and 3-amino-1,2-propanediol (Agricultural and Biological Chemistry; vol. 49; nb. 5; (1985); p. 1509-1512).

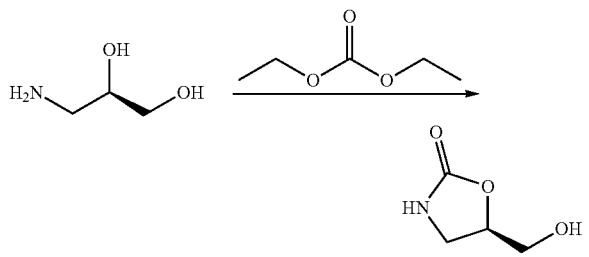

The carbonylation reagents are used to synthesize oxazolidinone in this method, which has a rapid reaction but a low yield, is difficult for the product to be purified, and is not suitable for industrial production.

It is reported in a literature (Tetrahedron: Asymmetry; vol. 6; nb. 5; (1995); p. 1181-1190) that benzyl (R)-2-oxooxazolidinone-5-carboxylate can be reduced to oxazolidinone by sodium borohydride in ethanol, as shown in the following formula.

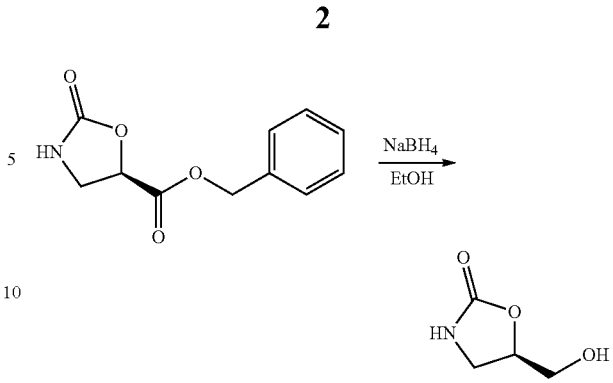

It is reported in another literature (Tetrahedron Asymmetry; vol. 16; nb. 8; (2005); p. 1485-1494) that (R)-5-(hydroxymethyl)oxazolidinone can be obtained by debenzylation of 4-methoxy-protected oxazolidinones under the action of ceric ammonium nitrate.

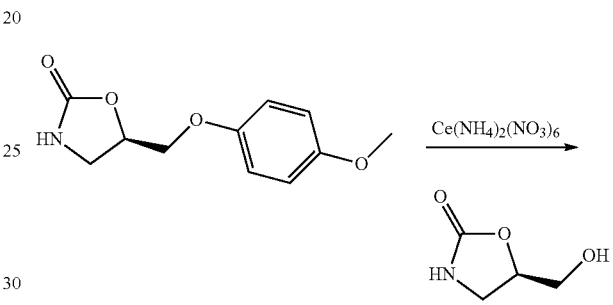

The above methods for synthesizing oxazolidinone by deprotection are chemically simple and feasible, but the yield is low and the product is not easy to purify. In particular, it is required to use the expensive ceric ammonium nitrate, which results in relatively high cost and difficulty of removal.

In summary, in the current synthesizing methods, the yield is low, the product is difficult to be purified and it is difficult for the industrial production. Especially, there is no effective control over the chirality of oxazolidinone.

SUMMARY OF THE INVENTION

The invention aims to provide a method for preparing oxazolidinone with low production cost, simple operation, high yield and purity, controllable chirality, and being suitable for industrial production. In particular, it relates to a novel method for preparing oxazolidinone by using novel intermediates.

The invention provides a method for preparing compound M oxazolidinone intermediate according to the following reaction formula:

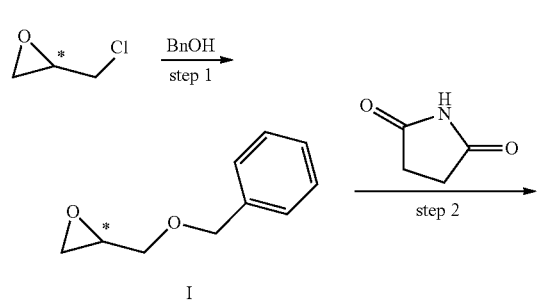

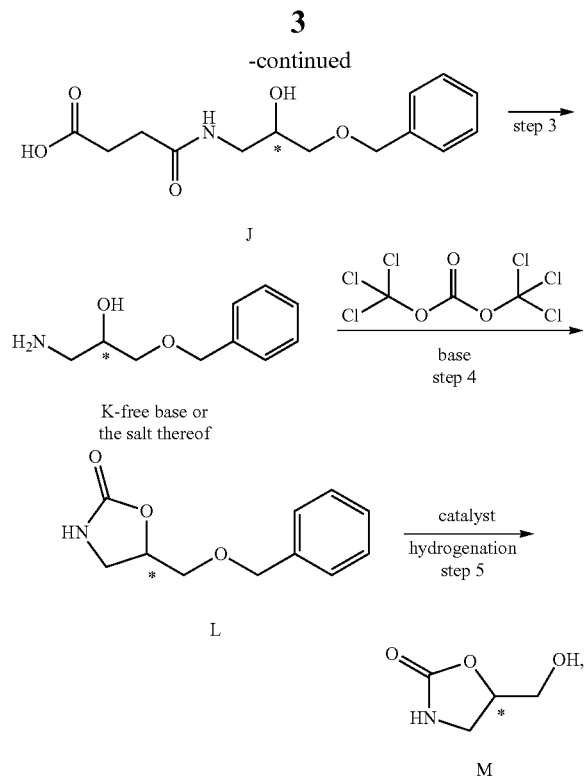

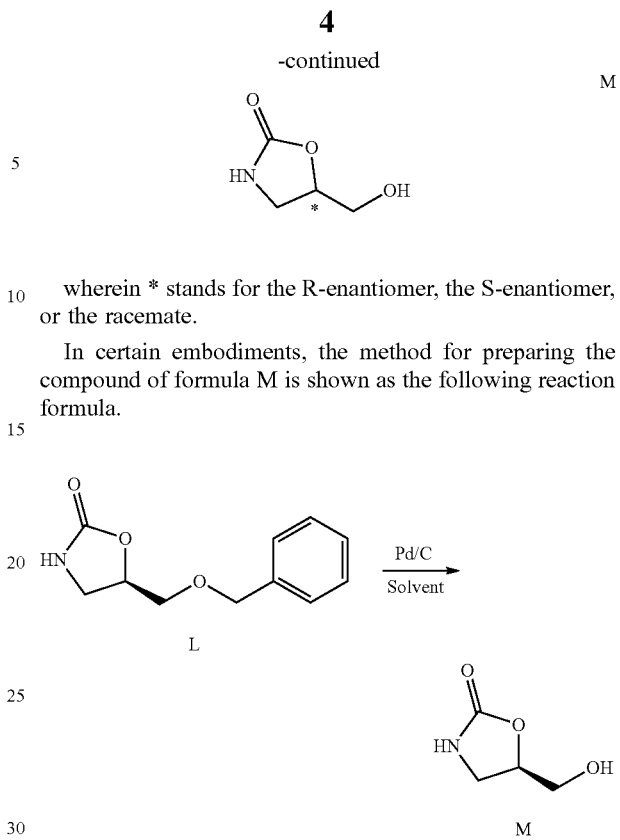

wherein * stands for the R-enantiomer, the S-enantiomer, or the racemate.

In certain embodiments, the method for preparing the compound of formula M is shown as the following reaction formula.

wherein the compound I, compound J, or compound L can be directly subjected to a "one-pot" reaction without being separated, and the compound K salt is selected from the group consisting of the corresponding hydrochloride, sulfate, malate, tartrate, p-toluenesulfonate or lactate; and wherein * stands for the R-enantiomer, the S-enantiomer, or the racemate.

The present invention provides a method for preparing compound M oxazolidinone intermediate, comprising catalytically hydrogenating compound L in the presence of a catalyst to obtain compound M:

The hydrogenation is performed in the presence of a transition metal catalyst, such as Pd(OH)$_2$/C, Pd/C, Rh/C, or Pt/C, preferably Pd(OH)$_2$/C. Besides using the metal catalyst alone, in some cases, it is also possible to carry out the reaction in the presence of acid, for example hydrochloric acid, nitric acid, acetic acid, sulfuric acid, phosphoric acid or amino acids to promote the reaction.

Usually, the solvent used in the catalytic hydrogenation reaction can be selected from the group consisting of ethers and alcohols solvents, preferably tetrahydrofuran, methyltetrahydrofuran, methanol, ethanol, isopropanol, ethyl acetate, and dioxane, more preferably methanol and tetrahydrofuran; and the reaction temperature is about 40-60° C.

The present invention provides a method for preparing compound M oxazolidinone intermediate according to the following reaction formula:

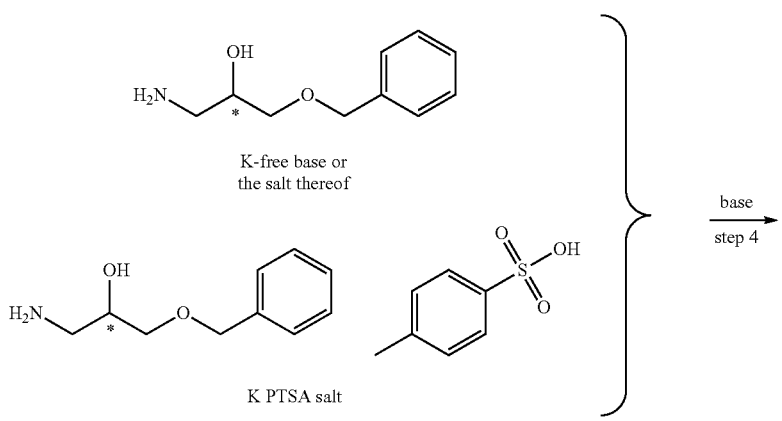

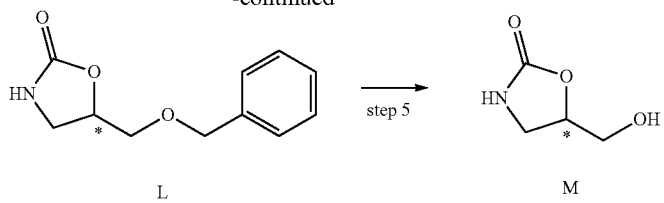

wherein * stands for the R-enantiomer, the S-enantiomer, or the racemate.

The compound L can be produced from the reaction of compound K-free base (also referred to as "freebase" in the present invention) or its hydrochloride, sulfate, malate, tartrate, p-toluenesulfonate or lactate, preferably p-toluenesulfonate (PTSA) or tartrate, with triphosgene in the presence of a base, wherein the compound L can be subjected to a catalytic hydrogenation in the presence of a catalyst by using "one-pot method", without being separated and purified, to provide the compound M.

The catalyst used in the catalytic hydrogenation for preparing the compound M from the compound L is a transition metal catalyst selected from the group consisting of Pd/C, Pd(OH)$_2$/C, Rh/C and Pt/C, preferably Pd(OH)$_2$/C, and the solvent for the hydrogenation reaction can be selected from the group consisting of ethers and alcohols solvents, preferably tetrahydrofuran, methyltetrahydrofuran, methanol, ethanol, isopropanol, ethyl acetate, and dioxane, more preferably methanol and tetrahydrofuran.

In the method for preparing compound M oxazolidinone intermediate according to the present invention, the base used in step 4 is selected from the group consisting of potassium carbonate, sodium carbonate, cesium carbonate, cesium fluoride, potassium acetate, sodium hydroxide, potassium hydroxide, potassium phosphate or sodium phosphate, preferably potassium carbonate and sodium carbonate. The solvent used in step 4 is preferably tetrahydrofuran, methyltetrahydrofuran and dichloromethane, and more preferably dichloromethane.

In a specific preferred embodiment according to the present invention, when the chiral carbon atom to which hydroxyl is attached in the K-free base is R type or S type, the chirality in the compound L will not be changed, i.e. the chirality is maintained. That is to say, when the compound K is converted into the compound L, the corresponding chiral center will be maintained, as shown in the following formula.

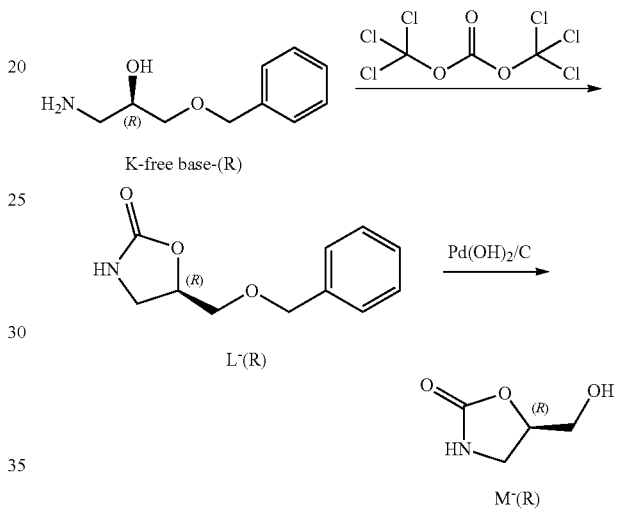

In a specific embodiment, the reaction solvent system is DCM-K$_2$CO$_3$ aqueous solution and the reaction temperature is 0-40° C., preferably 10-25° C.

In a specific embodiment, the K-free base in the R configuration is used to synthesize the compound M, in which the chiral configuration of the chiral center of the compound M is maintained, as shown in the following formula.

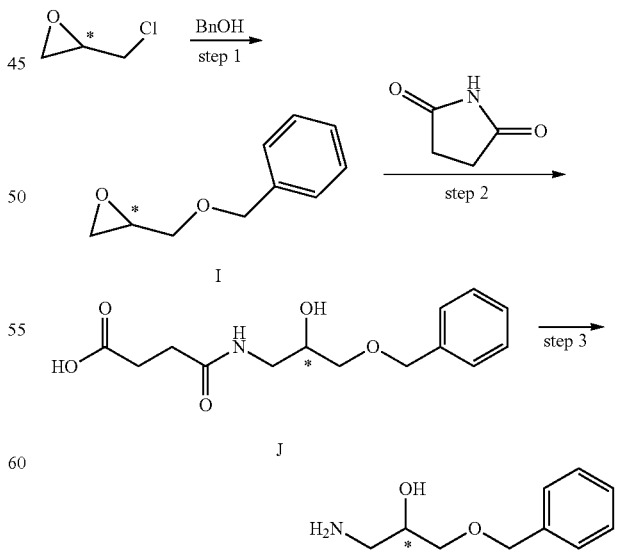

The present invention further provides a method for preparing compound K-free base or K salt according to the following formula,

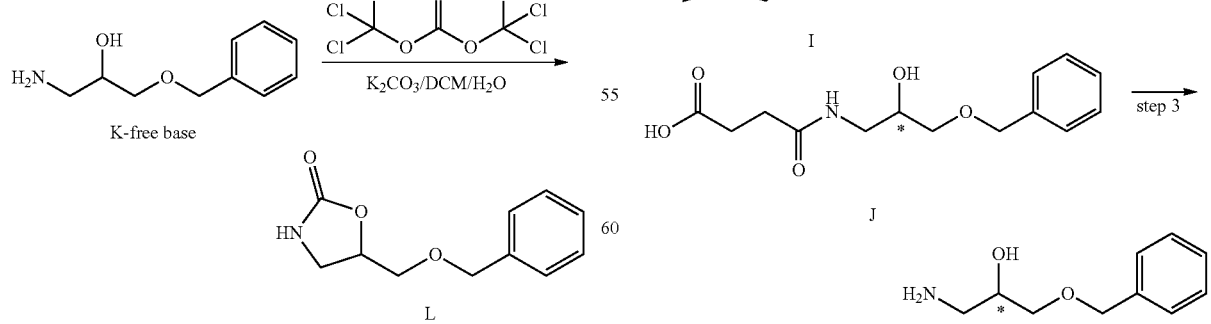

wherein * stands for the R-enantiomer, the S-enantiomer, or the racemate, the method comprising the following steps:

(1) reacting epichlorohydrin with benzyl alcohol under the presence of a phase transfer catalyst and a base to obtain compound I, wherein the compound I can be directly subjected to further reaction without being separated;

(2) reacting the compound I with succinimide under the presence of a base to obtain compound J, wherein the compound J can be directly subjected to further reaction without being separated; and (3) hydrolyzing the compound J in the condition of a strong base to obtain the compound K-free base, or salifying the compound K-free base in an organic solvent (preferably with p-toluenesulfonic acid or tartaric acid) without being separated and purified to obtain compound K salt.

The salt of compound K is selected from the group consisting of the corresponding hydrochloride, sulfate, malate, tartrate, p-toluenesulfonate or lactate; preferably p-toluenesulfonate and tartrate.

The phase transfer catalyst used in step (1) according to the present invention is selected from the group consisting of tetrabutylammonium bromide, tetrabutylammonium fluoride or tetrabutylammonium hydroxide, preferably tetrabutylammonium bromide; and the reaction of step (1) is performed without a solvent or in an organic solvent or in a mixed solvent of an organic solvent and water, wherein the organic solvent is preferably dichloromethane.

The base used in step (1) or step (2) is generally selected from the group consisting of potassium carbonate, sodium carbonate, cesium carbonate, cesium fluoride, potassium acetate, sodium hydroxide, potassium hydroxide, potassium phosphate or sodium phosphate, and preferably aqueous solution of sodium hydroxide, aqueous solution of potassium hydroxide, potassium carbonate, and sodium carbonate.

The reaction solvent used in step (2) according to the present invention is a mixed solvent system of an organic solvent and water, wherein the organic solvent can be selected from the group consisting of MeOH, DMF, THF, methyltetrahydrofuran, dichloromethane, DMSO, ACN, EtOH, and iPrOH, preferably EtOH and MeOH; and the reaction temperature in step (2) is 10-60° C., preferably 25-40° C.

The strong base used in step (3) according to the present invention is selected from the group consisting of potassium carbonate, sodium carbonate, cesium carbonate, sodium hydroxide, potassium hydroxide, potassium phosphate or sodium phosphate, preferably potassium hydroxide and sodium hydroxide. The preferred reaction temperature in step (3) is 70-110° C., more preferably 90-100° C. The reaction solvent in step (3) is selected from the group consisting of water or other high-boiling point solvents, or a combination thereof, preferably water, wherein the other high-boiling point solvents are selected from the group consisting of dioxane, DMF, or DMSO. The organic solvent for salifying in step (3) is any one selected from the group consisting of methanol, ethanol, isopropanol, dimethylformamide, tetrahydrofuran, methyltetrahydrofuran, dichloromethane, ethyl acetate, and isopropyl acetate or a mixed solvent thereof, preferably isopropyl acetate, or a mixed solvent of isopropyl acetate and ethanol.

In a preferred embodiment according to the present invention, epichlorohydrin H is reacted with benzyl alcohol in alkaline condition to produce compound I as shown in the following formula.

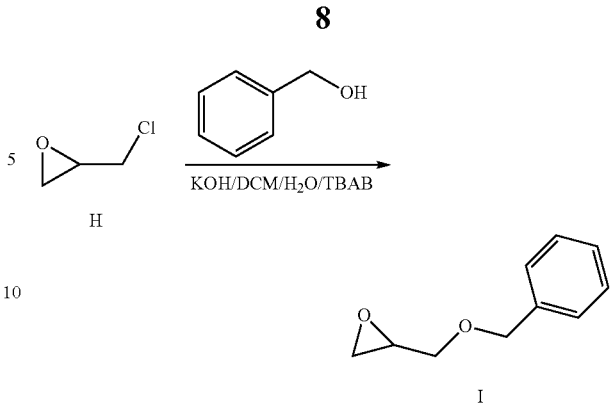

In a specific embodiment, the reaction catalyst is tetrabutylammonium bromide TBAB; the reaction solvent system is DCM-KOH aqueous solution, wherein the concentration of KOH aqueous solution is 20-60%, preferably 45-50%; and the reaction temperature is 0-40° C., preferably 5-15° C.

The compound I is subjected to a ring-opening reaction by the nucleophilic attack of succinimide to generate compound J, as shown in the following formula.

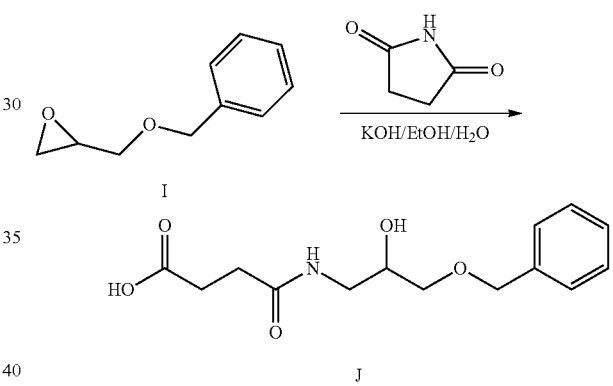

The reaction is carried out in the presence of a base. It can be $K_2CO_3$, $Na_2CO_3$, NaOH and $KHCO_3$, preferably NaOH, KOH, $K_2CO_3$ and $Na_2CO_3$.

The compound J is deprotected in the presence of a strong base to form compound K-free base as shown in the following formula.

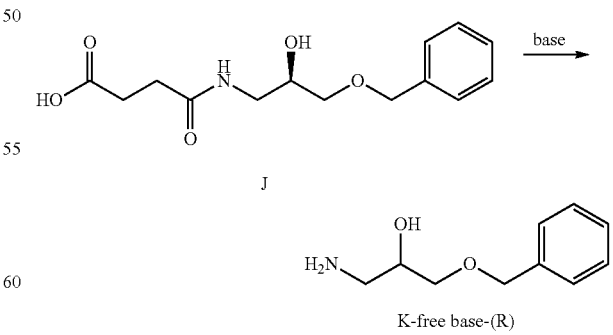

In a specific embodiment, the solvent is water or other high boiling point solvents such as dioxane, DMF, and DMSO, preferably water; and the reaction temperature is 70-110° C., preferably 90-100° C.

Alternatively, the K-free base can form a salt with an acid, such as hydrochloric acid, sulfuric acid, malic acid, tartaric acid, p-toluenesulfonic acid, and lactic acid, preferably p-toluenesulfonic acid and tartaric acid.

In certain specific embodiments, the K-free base and p-toluenesulfonic acid can form compound K PTSA salt as shown in the following formula:

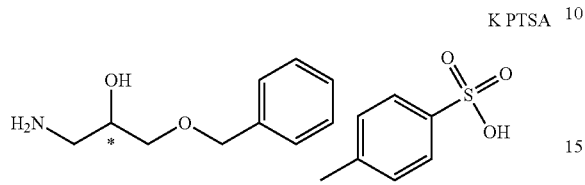

K PTSA wherein * stands for the R-enantiomer, the S-enantiomer, or the racemate.

In certain embodiments, the K-free base or K salt can be prepared in a "one-pot method", in which the intermediates I and J are not subjected to being separated and purified, as shown in the following formula.

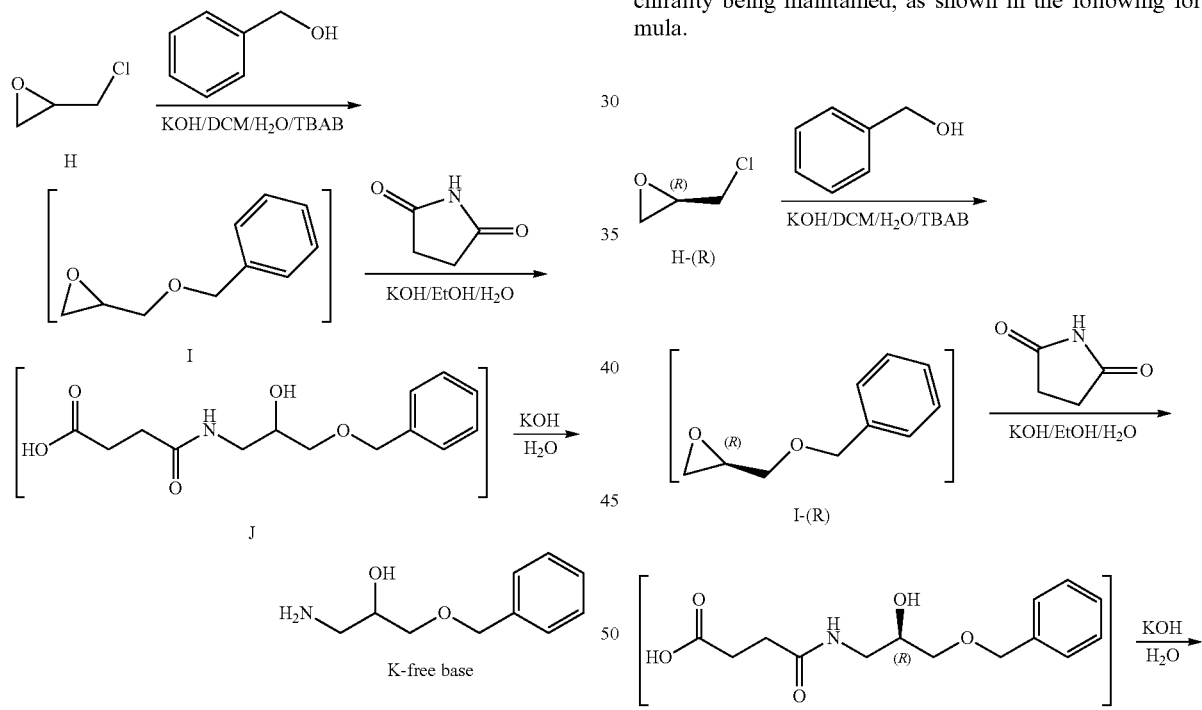

The K-free base is then purified by forming a salt, such as p-toluenesulfonate of K.

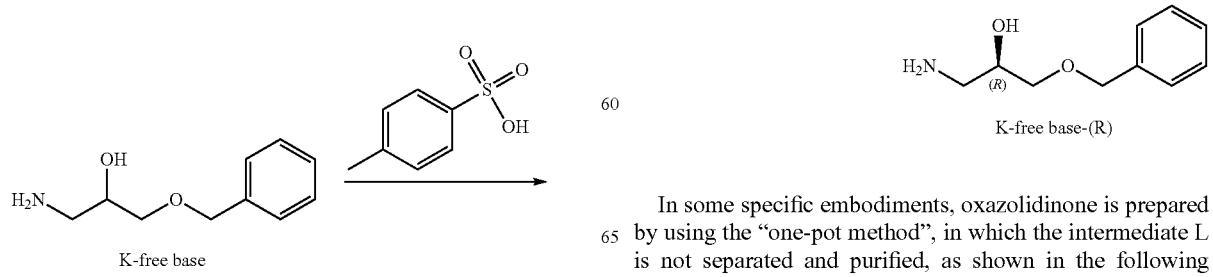

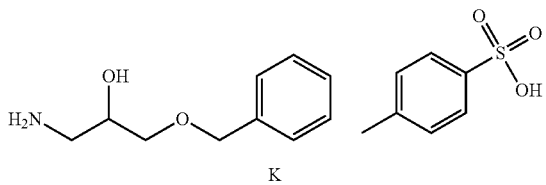

K

The solvent for forming salt is a conventional organic solvent such as toluene, acetonitrile, ethyl acetate, isopropyl acetate, methanol, ethanol, isopropyl alcohol, and tetrahydrofuran, or two or more mixed solvents of the above solvents, preferably mixed solvents of isopropyl acetate and ethanol.

The salt of compound K can be converted to K-free base by the addition of a base, with the chirality being maintained.

In the "one-pot method" for the preparation of K-free base or K-salt, the chiral purity of K-free base or K-salt can be simply and effectively controlled by controlling the chirality of epichlorohydrin. In certain specific embodiments, R-epichlorohydrin is used to obtain K-free base with the chirality being maintained, as shown in the following formula.

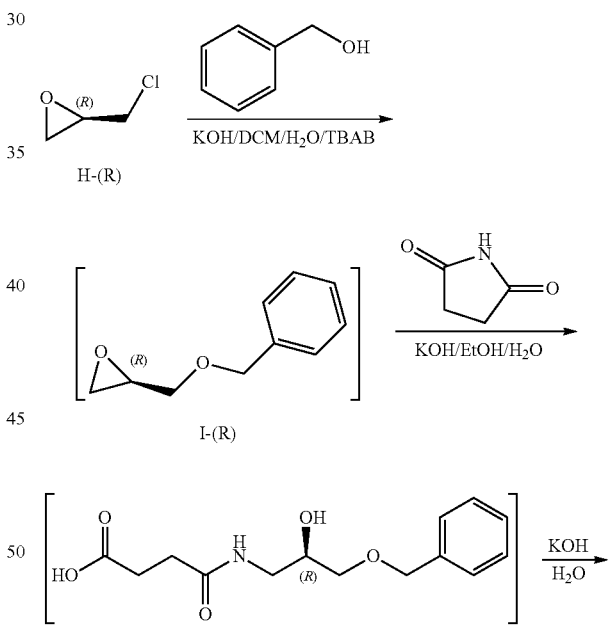

In some specific embodiments, oxazolidinone is prepared by using the "one-pot method", in which the intermediate L is not separated and purified, as shown in the following formula:

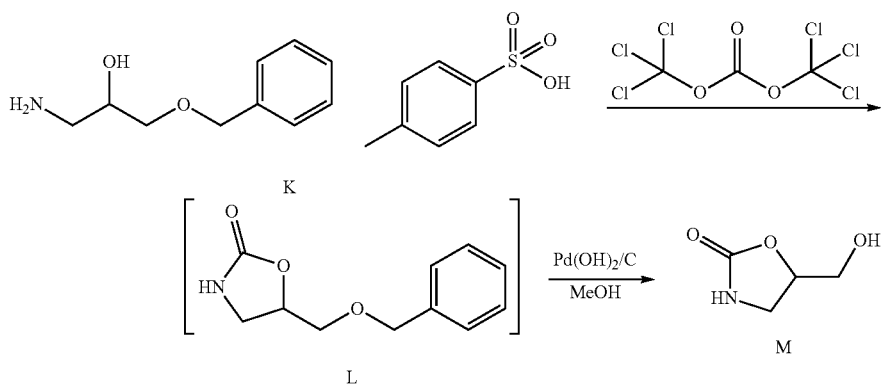

wherein the reaction conditions are similar to those of the above-mentioned similar reaction, and L is further subjected to a catalytic hydrogenation to generate M without being separated and purified.

The present invention also provides a compound J and a compound K salt:

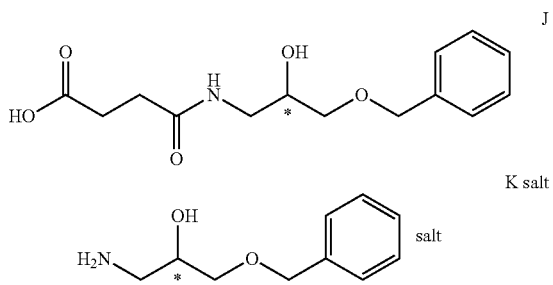

wherein the compound K salt is selected from the group consisting of the corresponding hydrochloride, sulfate, malate, tartrate, p-toluenesulfonate or lactate, preferably p-toluenesulfonate and tartrate; and wherein * stands for the R-enantiomer, the S-enantiomer, or the racemate.

The present invention also provides a compound M oxazolidinone intermediate obtained by the method according to the present invention. When the ee value of the starting material epichlorohydrin H in R type or S type is >98.0%, the enantiomer limit of the corresponding chiral compound K-free base or its salt is <0.10%.

The present invention also provides a method for preparing tedizolid by using the compound M oxazolidinone intermediate obtained according to the above-mentioned preparation method.

The beneficial technical effects of the present invention are as follows.

Compared with the prior art, the present invention provides a novel method for preparing oxazolidinone intermediate, which has the advantages of easy availability of raw materials, low cost, high yield of various steps, simple and easy operation of the process, and environmental protection and economic, being suitable for the industrial production. Among others, the "one pot method" is beneficial for improving the preparation and production efficiency and reducing energy consumption. Importantly, the chirality can be controlled in a simple manner. The chirally pure oxazolidinone can be obtained only by controlling the chirality of epichlorohydrin. In addition, the preparation method involved in the present invention requires using the key intermediates 4-((3-(benzyloxy)-2-hydroxypropyl)amino)-4-oxobutyric acid and compound K salt, such as (R)-1-amino-3-(benzyloxy)-2-propanol p-toluenesulfonate, the use of which allows the production route of oxazolidinone to be implemented.

DETAILED DESCRIPTION OF THE INVENTION

The implementation of the method of the present invention is illustrated by the following non-limiting examples.

Reagents are purchased from commercial sources and used upon receipt. The $^1$H nuclear magnetic resonance spectra are obtained at 400 MHz by Bruker AVANCE 400. Mass spectra are recorded by using Agilent HPLC 1260 Infinity and 6120 Duadrupole LC/MS.

For the purpose of showing the technical problems to be solved, the technical solutions and beneficial effects of the present invention more clearly, the present invention will be further described below in conjunction with specific examples. The specific examples as given are preferred examples of the present invention.

Example 1: Preparation of (R)-2-((benzyloxy)methyl)oxirane

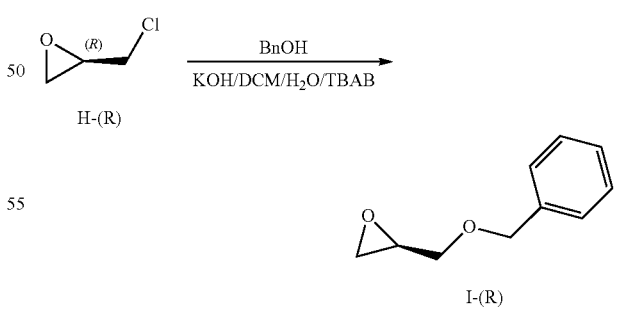

Water and KOH were added to a reaction kettle equipped with a mechanical agitator to form 50% w/w aqueous solution of KOH (20 kg), and cooled down to 0-10° C. While maintaining the temperature at 0-10° C., DCM (19 kg) was added, and benzyl alcohol (2.4 kg, 1 eq) was added under stirring. While maintaining the temperature at 0-10° C., TBAB (358 g, 0.05 eq) and KI (48 g, 2% w/w) were added in sequence. After completing the addition, the reaction mixture was stirred while maintaining the temperature at 0-10° C. While maintaining the temperature at 0-10° C., R-epichlorohydrin (2.88 kg, 1.4 eq) was dropwise added. After completing the addition, the reaction was performed while maintaining the temperature at 10±2° C. After reacting for 72 hours, the reaction was monitored by HPLC (the amount of benzyl alcohol <5%), stirring was stopped, and the temperature was raised to 20-25° C. It was allowed to stand for 1-2 hours and subjected to liquid separation. The resultant aqueous phase was extracted once with DCM (7.2 L). The DCM layers were combined, and distilled under reduced pressure (<35° C.) until no fractions were distilled off to provide 5.32 kg oily substance. The oily substance was distilled under reduced pressure (120-130° C., degree of vacuum<0.1 MPa), and the fractions were collected to obtain 2.55 kg oily substance, i.e. the product of (R)-2-((benzyloxy)methyl)oxirane. The yield was 70%. HPLC purity was 99.5%. GCMS [M]=164.1, NMR (CDCl₃, 400 MHz): 7.24-7.34 (m, 5H), 4.57 (q, 2H), 3.75 (dd, 1H), 3.42 (m, 1H), 3.18 (m, 1H), 2.78 (t, 1H), 2.60 (m, 1H).

Example 2: Preparation of (R)-4-((3-(benzyloxy)-2-hydroxypropyl)amino)-4-oxobutanoic acid

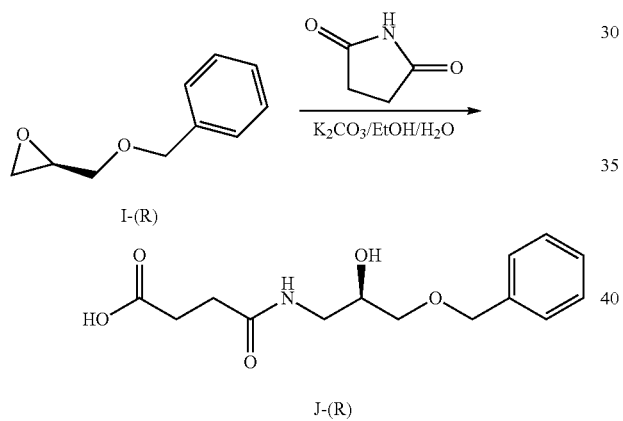

The oily substance I—(R) (200 g, 1 eq) was dissolved in EtOH (1 L), added with water (1 L), and stirred well. While keeping the temperature at <30° C., succinimide (362 g, 3 eq) and TBAB (4 g, 2% w/w) were added under stirring. While keeping the temperature at 10-30° C., K₂CO₃ (505 g, 3 eq) was added in batches within 2-3 hours. After completing the addition, the temperature was raised to 30±3° C. and the reaction was performed. After 24 hours, the amount of I—(R) was detected <5% by HPLC. The temperature was cooled down to room temperature. It was distilled under reduced pressure at 50-55° C. to distill off ethanol. The residue was added with 1 L of water, and stirred well. The aqueous phase was extracted twice with MTBE (500 mL), adjusted to pH 5-5.5 with 2M hydrochloric acid, added with a mixed solvent of ethyl acetate and isopropanol (500 mL, 10/1), and extracted twice. The organic phases were combined, dried over anhydrous sodium sulfate, and distilled under reduced pressure to remove the solvent, obtaining 137 g white solid product. The yield was 40%. HPLC showed a purity of 99.1%. LCMS [M+H]=282.2.

Example 3: Preparation of (R)-1-amino-3-(benzyloxy)-2-propanol

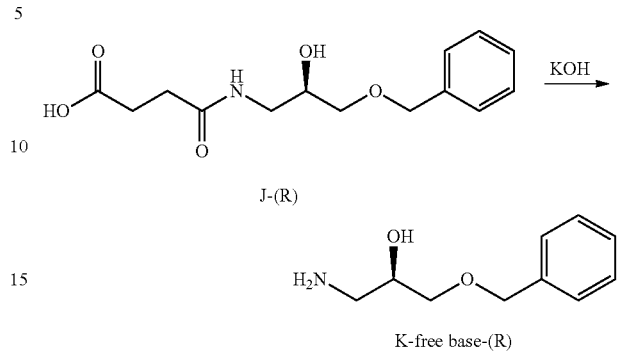

J-(R) (36.0 g, 1 eq) was added to water (180 g), and 50% KOH aqueous solution (42 g, 3 eq) was added dropwise. After completing the addition, the reaction mixture was heated to 95-100° C., kept temperature at 95-100° C., stirred and reacted for 20 hours. The middle-controlled analysis of HPLC showed the amount of J-(R)<5.0%. It was cooled down to 15-25° C., added with DCM (180 mL), and extracted for liquid separation. The aqueous phase was extracted once again with DCM (180 mL). The DCM phases were combined, washed once with 70 mL of 10% NaCl, and concentrated to remove DCM while keeping the temperature <35° C. until no fractions were distilled off to obtain an oily substance. The oily substance was dissolved in isopropyl acetate (180 mL), cooled down to −30° C., stirred for 1-2 hours, and filtered to obtain a white solid. The product was dried under vacuum at 20-30° C. to obtain 20 g K-free base-(R). The yield was 86%. HPLC showed a purity of 99.0%. LCMS [M+H]=181.9, NMR (CDCl₃, 400 MHz): 7.53 (br, 2H), 7.20-7.26 (m, 3H), 7.15-7.18 (m, 2H), 4.31 (q, 2H), 3.98 (m, 1H), 3.26 (d, 2H), 2.88 (m, 2H).

Example 4: Preparation of (R)-1-amino-3-(benzyloxy)-2-propanol p-toluenesulfonate

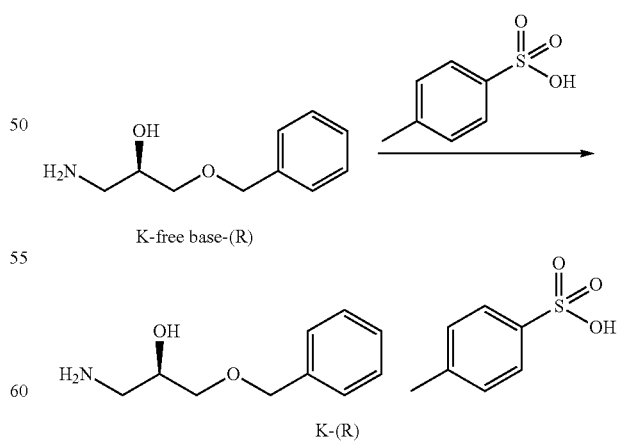

K-free base-(R) (21.0 g, 1 eq) was added to isopropyl acetate (420 mL), heated to 65-70° C., and stirred for completely dissolving. P-toluenesulfonic acid (19.95 g, 1 eq) was added, and stirred for completely dissolving while maintaining the temperature at 65-70° C. The solution was slowly cooled down to 20-30° C., stirred for 1-2 hours, and filtered. The filter cake was dried under vacuum at 45-50° C. to obtain 39.3 g K—(R). The yield was 96%. HPLC showed a purity of 99.8%. LCMS [M+H]=181.9, NMR (CDCl$_3$, 400 MHz): 7.74 (s, 1H), 7.72 (s, 1H), 7.53 (br, 2H), 7.20-7.26 (m, 3H), 7.15-7.18 (m, 2H), 7.03 (s, 1H), 7.71 (s, 1H), 4.31 (q, 2H), 3.98 (m, 1H), 3.26 (d, 2H), 2.88 (m, 2H), 2.25 (s, 3H).

Example 5: Preparation of (R)-5-((benzyloxy)methyl)oxazolidin-2-one

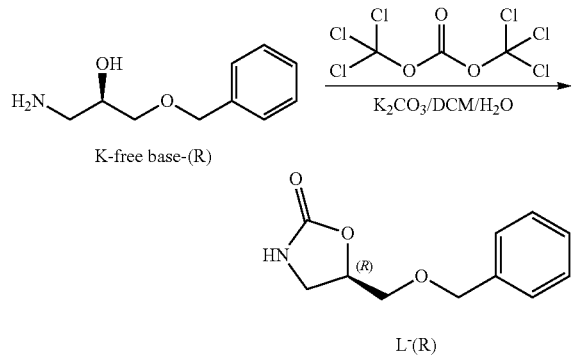

K-free base-(R) (100 g, 1 eq) was dissolved in DCM (1500 mL), added with 1500 mL aqueous solution containing Na$_2$CO$_3$ (153 g, 2 eq), cooled down to 0° C. While keeping the temperature at 0-10° C., DCM solution (400 mL) of triphosgene (65.5 g, 0.4 eq) was added. After completing the addition, the reaction was performed while keeping the temperature at 15-20° C. After 2-3 hours, the amount of K-free base-(R) was detected <1.0% by HPLC. 12 ml aqueous ammonia was added to adjust pH=8-9, stirred for 30 min, and stood for layering. The resultant aqueous phase was extracted once with DCM (300 ml), and stood for layering to obtain an organic phase. The organic phases were combined, and washed successively with water (250 ml, 2.5 V), 1N HCl (250 ml, 2.5 V), and 10% aq NaCl (250 ml, 2.5 V) to obtain an organic phase. The organic phase was adsorbed with 5% w/w activated carbon, stirred for 1 h, and filtered (aided by celite). The filtrate was concentrated to remove DCM until no fraction was distilled off (<35° C.). Methyl tert-butyl ether (300 mL) was added, cooled down to −30° C. to −50° C., stirred for crystallization for 1-2 hours, and filtered. The filter cake was dried under vacuum at 30-40° C. to obtain L-(R) (99.5 g). The yield was 87%. HPLC showed a purity of 99.5%. LCMS [M+H]=207.9, NMR (CDCl$_3$, 400 MHz): 7.26-7.37 (m, 5H), 6.19 (s, 1H), 4.76 (m, 1H), 4.59 (s, 2H), 3.60-3.64 (m, 3H), 3.45 (m, 1H).

Example 6: Preparation of (R)-5-(hydroxymethyl)oxazolidin-2-one

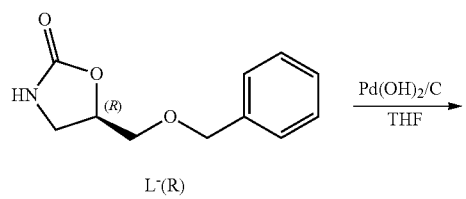

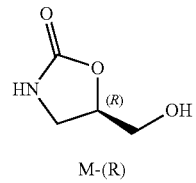

(R)-5-((benzyloxy)methyl)oxazolidin-2-one (15 g, 1 eq), tetrahydrofuran (150 mL) and Pd(OH)$_2$/C (1.5 g, 10% w/w) were added into a three-neck flask equipped with a stirrer. After replacing with hydrogen gas, the mixture was heated to 45° C., stirred and reacted for 3 hours while keeping this temperature. After the reaction was completed by monitoring by HPLC, the stirring was stopped. The resultant was filtered to remove Pd/C, and concentrated to remove tetrahydrofuran so as to obtain a colorless oily substance. The oily substance was added with ethyl acetate (150 mL), distilled off THF under reduced pressure to 45 mL, cooled down to room temperature, stirred for 3 hours for crystallization, and filtered. The filter cake was collected, and dried under vacuum at 30-40° C. to obtain 7.6 g white solid product. The yield was 90%. HPLC showed a purity of 98.8%. LCMS [M+H]=117.9, NMR (DMSO-d6, 400 MHz): 7.92 (s, 1H), 4.68-4.60 (m, 1H), 3.97-3.90 (m, 1H), 3.70 (br, 1H), 3.62-3.55 (m, 2H), 3.11-3.06 (m, 1H).

Example 7: Preparation of (R)-5-(hydroxymethyl)oxazolidin-2-one

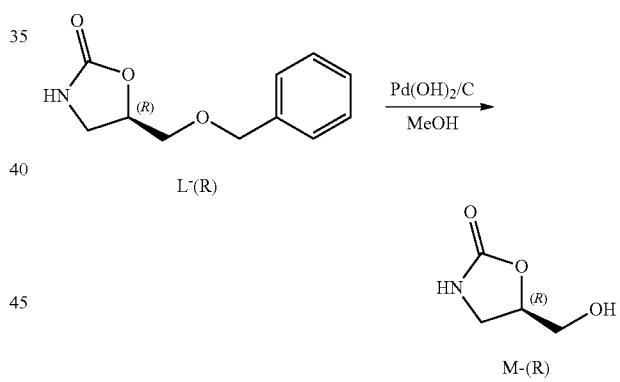

(R)-5-((benzyloxy)methyl)oxazolidin-2-one (200 g, 1 eq), methanol (2000 mL) and Pd(OH)$_2$/C (12 g, 6% w/w) were added into a three-neck flask equipped with a stirrer. After replacing with hydrogen gas, the reaction mixture was heated to 45° C., stirred and reacted for 7-9 hours while keeping at this temperature. After the reaction was completed by monitoring by HPLC, stirring was stopped. The resultant was filtered to remove Pd(OH)$_2$/C, and concentrated to dryness to remove methanol. Ethyl acetate (2000 mL) was added, distilled off methanol under reduced pressure to 600 mL, cooled down to room temperature, stirred for 2-3 hours for crystallization, and filtered. The filter cake was collected, and dried under vacuum at 30-40° C. to obtain 180 g white solid product. The yield was 90%. HPLC showed a purity of 99.4%.

LCMS [M+H]=117.9, NMR (DMSO-d6, 400 MHz): 7.92 (s, 1H), 4.68-4.60 (m, 1H), 3.97-3.90 (m, 1H), 3.70 (br, 1H), 3.62-3.55 (m, 2H), 3.11-3.06 (m, 1H).

Example 8: Preparation of (R)-1-amino-3-(benzyloxy)-2-propanol p-toluenesulfonate Via One Pot Method

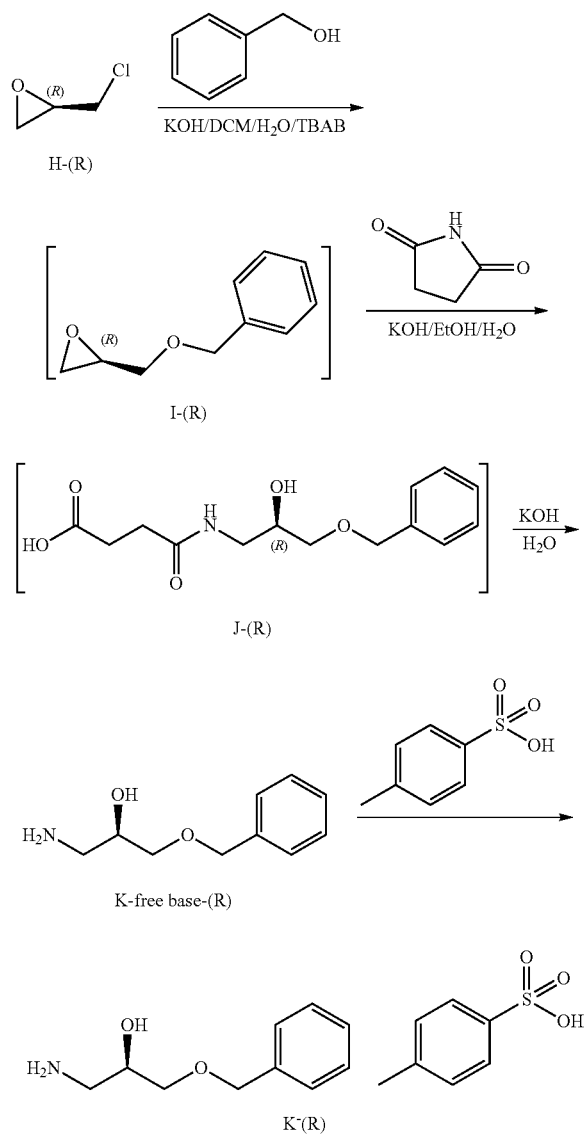

Water and KOH were added into a reaction kettle equipped with a mechanical agitator to form 50% w/w aqueous solution of KOH (1.2 L), and cooled down to 0-10° C. While maintaining the temperature at 0-10° C., DCM (1.2 L) was added, and benzyl alcohol (200 g, 1 eq) was added under stirring. While maintaining the temperature at 0-10° C., TBAB (10 g, 5 w/w) and KI (4 g, 2% w/w) were added in sequence. After completing the addition, the reaction mixture was stirred while maintaining the temperature at 0-10° C. While maintaining the temperature at 0-10° C., R-epichlorohydrin (240 g, 1.4 eq) was dropwise added. After completing the addition, the reaction was performed while maintaining the temperature at 10±2° C. After reacting for 72 hours, the reaction was monitored by HPLC (the amount of benzyl alcohol <5%), stirring was stopped, and the temperature was raised to 20-25° C. It was allowed to stand for 1-2 hours and subjected to liquid separation. The resultant aqueous phase was extracted once with DCM (1.2 L). The DCM layers were combined, and distilled under reduced pressure (<35° C.) until no fractions were distilled off to obtain 480 g oily substance. The yield was 75% as determined by external standard method.

The above oily substance was dissolved in EtOH (1 L), water (1 L) was added thereto, and stirred well. While keeping the temperature <30° C., succinimide (412 g, 3 eq) and TBAB (4.6 g, 2% w/w) were added under stirring. While keeping the temperature at 10-30° C., $K_2CO_3$ (575 g, 3 eq) was added in batches within 2-3 hours. After completing the addition, the temperature was raised to 30±3° C. and the reaction was performed. After 24 hours, the amount of I—(R) was detected <5% by HPLC, then the temperature was cooled down to room temperature, and ethanol was distilled off under reduced pressure at 50-55° C. The residue was added with 500 mL of water, and raised to a temperature of 70-80° C. under stirring. After stirring for 1-2 hours, 50% aqueous solution of KOH (700 g KOH, 9 eq) was dropwise added while keeping the temperature at 70-100° C. After completing the addition, the system was heated to 95-100° C., and reacted for 20 hours under stirring while maintaining the temperature at 95-100° C. The middle-controlled analysis of HPLC showed the amount of J-(R)<5.0%. The resultant was cooled down to 15-25° C., added with DCM (1 L), and subjected to extraction and liquid separation. The aqueous phase was extracted once again with DCM (500 mL). The DCM phases were combined, washed once with 500 mL 10% NaCl, and concentrated to remove DCM while keeping the temperature <35° C. until no fraction was distilled off to obtain an oily substance.

Isopropyl acetate (1.2 L) and ethanol (100 ml) were added by suction to the above oily substance, heated to 65-70° C., and stirred. After completely dissolving, p-toluenesulfonic acid (212 g, 1 eq) was added, and stirred while keeping the temperature at 65-70° C. After completely dissolving, the system was slowly cooled down to 20-30° C., stirred for 1-2 hours, and filtered. The filter cake was dried under vacuum at 45-50° C. to obtain 359 g of crude K—(R). The yield was 73%. HPLC showed a purity of 99.5%, with the amount of enantiomer of K—(S) being 0.25%.

Isopropyl acetate (3.6 L) and ethanol (300 ml) were added by suction to 300 g of the above crude K—(R), heated to 65-70° C., and stirred. After completely dissolving, the system was slowly cooled down to 20-30° C., stirred for 1-2 hours, and filtered. The filter cake was dried under vacuum at 45-50° C. to obtain 288 g of K—(R). The yield of crystallization was 96%. HPLC showed a purity of 99.8%, with the amount of enantiomer of K—(S)<0.10%. NMR ($CDCl_3$, 400 MHz): 7.74 (s, 1H), 7.72 (s, 1H), 7.53 (br, 2H), 7.20-7.26 (m, 3H), 7.15-7.18 (m, 2H), 7.03 (s, 1H), 7.71 (s, 1H), 4.31 (q, 2H), 3.98 (m, 1H), 3.26 (d, 2H), 2.88 (m, 2H), 2.25 (s, 3H).

Example 9: Preparation of (R)-1-amino-3-(benzyloxy)-2-propanol Via One Pot Method

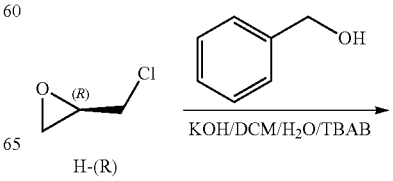

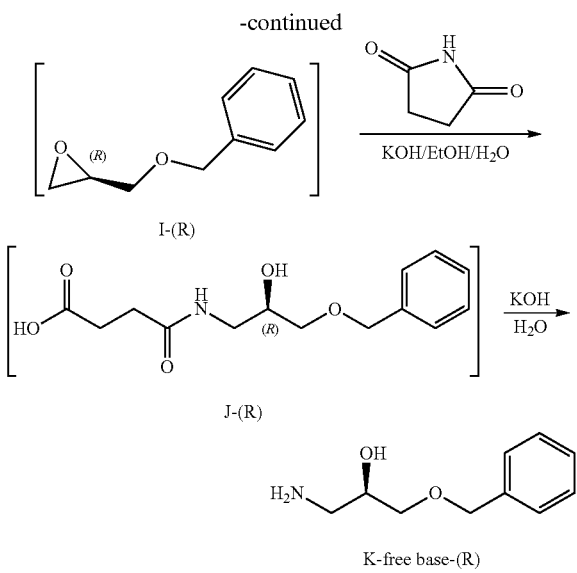

Water and KOH were added into a reaction kettle equipped with a mechanical agitator to form 50% w/w aqueous solution of KOH (1.2 L), and cooled down to 0-10° C. While maintaining the temperature at 0-10° C., DCM (1.2 L) was added, and benzyl alcohol (200 g, 1 eq) was added under stirring. While maintaining the temperature at 0-10° C., TBAB (10 g, 5 w/w) and KI (4 g, 2% w/w) were added in sequence. After completing the addition, the reaction mixture was stirred while maintaining the temperature at 0-10° C. While maintaining the temperature at 0-10° C., R-epichlorohydrin (240 g, 1.4 eq) was dropwise added. After completing the addition, the reaction was performed while maintaining the temperature at 10±2° C. After reacting for 72 hours, the reaction was monitored by HPLC (the amount of benzyl alcohol <5%), stirring was stopped, and the temperature was raised to 20-25° C. It was allowed to stand for 1-2 hours and subjected to liquid separation. The resultant aqueous phase was extracted once with DCM (1.2 L). The DCM layers were combined, and distilled under reduced pressure (<35° C.) until no fractions were distilled off to obtain 480 g oily substance. The yield was 75% as determined by external standard method.

The above oily substance was dissolved in EtOH (1 L), water (1 L) was added thereto, and stirred well. While keeping the temperature <30° C., succinimide (412 g, 3 eq) and TBAB (4.6 g, 2% w/w) were added under stirring. While keeping the temperature at 10-30° C., $K_2CO_3$ (575 g, 3 eq) was added in batches within 2-3 hours. After completing the addition, the temperature was raised to 30±3° C. and the reaction was performed. After 24 hours, the amount of I—(R) was detected <5% by HPLC, then the temperature was cooled down to room temperature, and ethanol was distilled off under reduced pressure at 50-55° C. The residue was added with 500 mL of water, and raised to a temperature of 70-80° C. under stirring. After stirring for 1-2 hours, 50% aqueous solution of KOH (700 g KOH, 9 eq) was dropwise added while keeping the temperature at 70-100° C. After completing the addition, the system was heated to 95-100° C., and reacted for 20 hours under stirring while maintaining the temperature at 95-100° C. The middle-controlled analysis of HPLC showed the amount of J-(R)<5.0%. The resultant was cooled down to 15-25° C., added with DCM (1 L), and subjected to extraction and liquid separation. The aqueous phase was extracted once again with DCM (500 mL). The DCM phases were combined, washed once with 500 mL 10% NaCl, and concentrated to remove DCM while keeping the temperature <35° C. until no fraction was distilled off to obtain an oily substance.

Methyl tert-butyl ether (2.2 L) was added by suction to the above oily substance, heated to 40-50° C. under stirring, slowly cooled down to −20° C. to −30° C., stirred for 1-2 hours for crystallization, and filtered. The filter cake was dried under vacuum at 30-40° C. to obtain 186 g white solid. The yield was 74%. HPLC showed a purity of 99.3%, with the amount of enantiomer of K—(S) being 0.16%.

150 g of the above crude product was dissolved in ethanol (300 mL), and cooled down to 0-10° C. Methyl tert-butyl ether (1500 mL) was slowly added dropwise. After completing the addition, the system was cooled down to −20° C. to −30° C., stirred for 1-2 hours for crystallization, and filtered. The filter cake was dried under vacuum at 30-40° C. to obtain 135 g white solid. The yield was 90%. HPLC showed a purity of 99.9%, with the amount of enantiomer K—(S)<0.10%. LCMS [M+H]=181.9, NMR ($CDCl_3$, 400 MHz): 7.53 (br, 2H), 7.20-7.26 (m, 3H), 7.15-7.18 (m, 2H), 4.31 (q, 2H), 3.98 (m, 1H), 3.26 (d, 2H), 2.88 (m, 2H).

Example 10: Preparation of (R)-5-(hydroxymethyl)oxazolidin-2-one Via One Pot Method

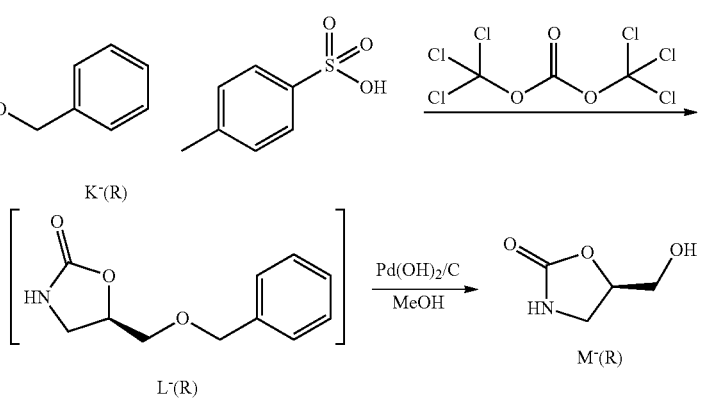

K—(R) (200 g, 1 eq) was dissolved in DCM (2000 mL), added with aqueous solution (1000 mL) of KOH (47.6 g, 1.5 eq), and stirred for 1-2 hours. NaCl (150 g) was added, stirred for 1-2 hours, and stood for phase separation. DCM phase was separated. The aqueous phase was extracted with DCM (400 ml). The DCM phases were combined, washed with 500 ml saturated brine, and stood for phase separation to obtain an organic phase. The organic phase was concentrated at 20-30° C., and distilled off DCM to 1000 mL to obtain a DCM solution of K-free base-(R). 600 mL aqueous solution of Na$_2$CO$_3$ (2 eq) was added to the DCM (1000 mL) solution of K-free base-(R), and DCM solution (400 mL) of triphosgene (67 g, 0.4 eq) was dropwise added at 0-10° C. After completing the addition, the system was reacted while keeping at a temperature of 15-20° C. After 2-3 hours, the amount of K-free base-(R) was detected <1.0% by HPLC. 25 mL aqueous ammonia was added to adjust pH=8-9, stirred for 30 min, and stood for phase separation. The aqueous phase was extracted once with DCM (600 ml), and stood for phase separation to obtain an organic phase. The organic phases were combined, and washed successively with water (500 mL), 1N HCl (500 mL), and 10% aq NaCl (500 mL) to obtain an organic phase. The organic phase was adsorbed by 5% w/w activated carbon, stirred for 1 h, and filtered (aided by celite). The filtrate was concentrated to remove DCM until no fractions were distilled off (<35° C.), obtaining 137 g oily substance, that is L-(R). The yield was 90% as determined by external standard method.

Methanol (1000 mL) was added by suction to the above oily substance, and distilled under reduced pressure while keeping the temperature at 30-35° C. to remove dichloromethane to a volume of 500 mL 1000 mL methanol was added by suction again, and distilled under reduced pressure to 1000 mL Pd(OH)$_2$/C (6 g) was added, replaced with hydrogen, heated to 45° C., kept this temperature, stirred and reacted for 10 hours. HPLC monitoring showed the reaction was completed. After stopping stirring, the system was filtered to remove Pd(OH)$_2$/C, and concentrated for removing methanol to obtain a colorless oily substance. Ethyl acetate (1000 mL) was added, distilled under reduced pressure to remove methanol until the volume of methanol was 300 mL, cooled down to 0-10° C., stirred for 2-3 hours for crystallization, and filtered. The filter cake was collected, and dried under vacuum at 30-40° C. to obtain 56 g white solid product. The yield was 85%. GC showed a purity of 99.6%, with the amount of enantiomer M-(S)<0.1%. LCMS [M+H]=117.9, NMR (DMSO-d6, 400 MHz): 7.92 (s, 1H), 4.68-4.60 (m, 1H), 3.97-3.90 (m, 1H), 3.70 (br, 1H), 3.62-3.55 (m, 2H), 3.11-3.06 (m, 1H).

Example 11: Preparation of (R)-5-(hydroxymethyl)oxazolidin-2-one Via One Pot Method

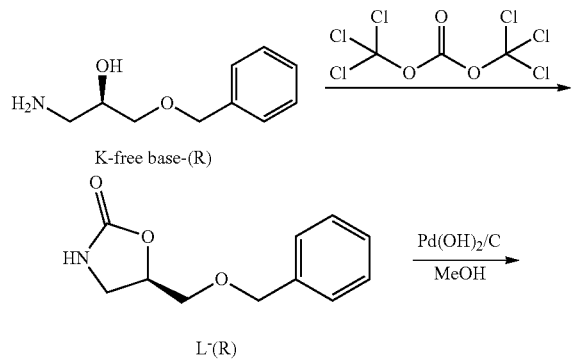

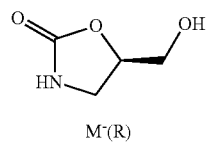

K-free base-(R) (100 g, 1 eq) was dissolved in DCM (1500 mL), added with 1500 mL aqueous solution containing Na$_2$CO$_3$ (153 g, 2 eq), and cooled down to 0° C. While keeping the temperature at 0-10° C., DCM solution (400 mL) of triphosgene (65.5 g, 0.4 eq) was added dropwise. After completing the addition, the reaction was performed while keeping the temperature at 15-20° C. After 2-3 hours, the amount of K-free base-(R) was detected <1.0% by HPLC. 12 ml aqueous ammonia was added to adjust pH=8-9, stirred for 30 min, and stood for phase separation. The aqueous phase was extracted once with DCM (300 ml), and stood for phase separation to obtain an organic phase. The organic phases were combined, washed successively with water (250 ml), 1N HCl (250 ml), and 10% aq NaCl (250 ml) to obtain an organic phase. The organic phase was adsorbed by 5% w/w activated carbon, stirred for 1 h, and filtered (aided by celite). The filtrate was concentrated to remove DCM until no fractions were distilled off (<35° C.) to obtain 134 g oily substance, that is L-(R). The yield was 90% as determined by external standard. Methanol (1000 mL) was added by suction to the above oily substance, and distilled under reduced pressure while keeping the temperature at 30-35° C. to remove dichloromethane until 500 mL dichloromethane was remained. 1000 mL methanol was added by suction again, and distilled under reduced pressure to 1000 mL Pd(OH)$_2$/C (6 g) was added, replaced with hydrogen, heated to 45° C., kept this temperature, stirred and reacted for 10 hours. HPLC monitoring showed that the reaction was completed. After stopping stirring, the system was filtered to remove Pd(OH)$_2$/C, and concentrated for removing methanol to obtain a colorless oily substance. Ethyl acetate (1000 mL) was added, distilled under reduced pressure to remove methanol until 300 mL methanol was remained, cooled down to 0-10° C., stirred for 2-3 hours for crystallization, and filtered. The filter cake was collected and dried under vacuum at 30-40° C. to obtain 53 g white solid product. The yield was 82%. The GC showed a purity of 99.9%, with the amount of enantiomer M-(S)<0.1%. LCMS [M+H]=117.9, NMR (DMSO-d6, 400 MHz): 7.92 (s, 1H), 4.68-4.60 (m, 1H), 3.97-3.90 (m, 1H), 3.70 (br, 1H), 3.62-3.55 (m, 2H), 3.11-3.06 (m, 1H).

The foregoing examples are merely preferred examples of the present invention and are not intended to limit the present invention. Any modifications, equivalent substitutions and improvements made within the spirit and principle of the present invention shall be included in the scope of protection of the present invention.

The invention claimed is:

1. A method for preparing compound M oxazolidinone intermediate, comprising catalytically hydrogenating compound L in the presence of a solvent and a catalyst to obtain compound M:

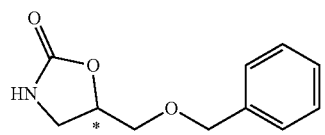

-continued

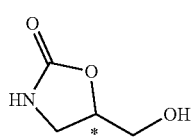

wherein * stands for the R-enantiomer, the S-enantiomer, or the racemate.

2. The method according to claim 1, wherein a compound K-free base or a salt thereof is reacted with triphosgene in the presence of a second solvent and a base to produce compound L, wherein the compound L can be subjected to a catalytic hydrogenation in the presence of a catalyst by using "one-pot method", without being separated and purified, to provide compound M,

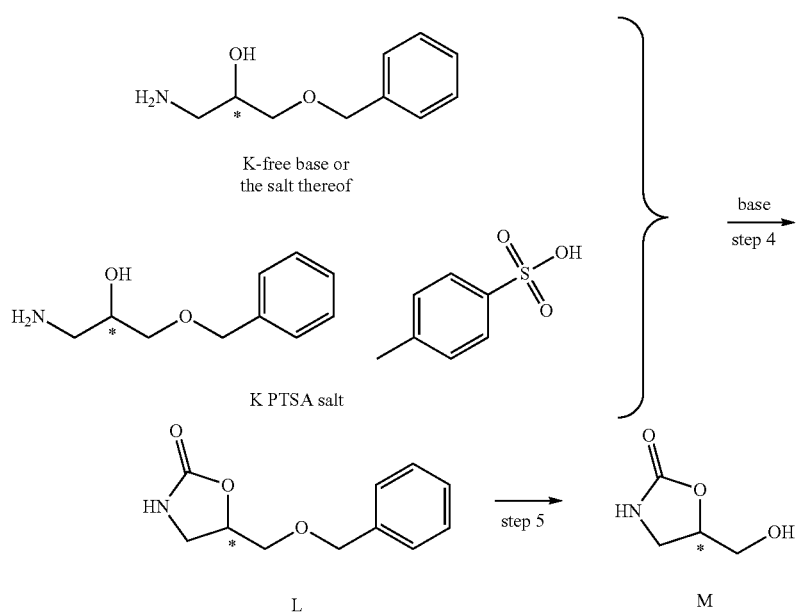

wherein the compound K salt is selected from the group consisting of hydrochloride, sulfate, malate, tartrate, p-toluenesulfonate or lactate; and
wherein * stands for the R-enantiomer, the S-enantiomer, or the racemate.

3. The method according to claim 1, wherein the catalyst used in the catalytic hydrogenation for preparing the compound M from the compound L is a transition metal catalyst selected from the group consisting of Pd/C, Pd(OH)$_2$/C, Rh/C or Pt/C.

4. The method according to claim 1, wherein the solvent used in the catalytic hydrogenation for preparing the compound M from the compound L is selected from the group consisting of ethers and alcohols solvents.

5. The method according to claim 2, wherein the base used in step 4 is selected from the group consisting of potassium carbonate, sodium carbonate, cesium carbonate, cesium fluoride, potassium acetate, sodium hydroxide, potassium hydroxide, potassium phosphate or sodium phosphate.

6. The method according to claim 2, wherein the second solvent used in step 4 is tetrahydrofuran, methyltetrahydrofuran or dichloromethane.

7. The method according to claim 2, wherein the compound K-free base or salt thereof is prepared according to the following reaction formula,

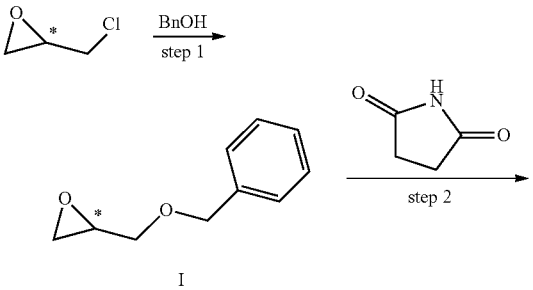

wherein * stands for the R-enantiomer, the S-enantiomer, or the racemate, and
wherein the compound K salt is selected from the group consisting of hydrochloride, sulfate, malate, tartrate, p-toluenesulfonate or lactate;
the method comprising the following steps:
step 1: reacting epichlorohydrin with benzyl alcohol under the presence of a phase transfer catalyst and a base to obtain compound I, wherein the compound I can be directly subjected to further reaction without being separated;

step 2: reacting the compound I with succinimide under the presence of a reaction solvent and a base to obtain compound J, wherein the compound J can be directly subjected to further reaction without being separated; and step 3: hydrolyzing the compound J in a second reaction solvent in the condition of a strong base to obtain the compound K-free base, or salifying the compound K-free base in an organic solvent without being separated and purified to obtain compound K salt.

8. The method according to claim 7, wherein the phase transfer catalyst in step 1 is selected from the group consisting of tetrabutylammonium bromide, tetrabutylammonium fluoride or tetrabutylammonium hydroxide; and the reaction of step 1 is performed without a solvent or in an organic solvent.

9. The method according to claim 7, wherein the base used in step 1 or step 2 is selected from the group consisting of potassium carbonate, sodium carbonate, cesium carbonate, cesium fluoride, potassium acetate, sodium hydroxide, potassium hydroxide, potassium phosphate or sodium phosphate.

10. The method according to claim 7, wherein the reaction solvent in step 2 is methanol, ethanol, dimethylformamide, tetrahydrofuran, methyltetrahydrofuran, dichloromethane; and the reaction in step 2 is performed at a temperature of 10-60° C.

11. The method according to claim 7, wherein the strong base used in step 3 is selected from the group consisting of potassium carbonate, sodium carbonate, cesium carbonate, sodium hydroxide, potassium hydroxide, potassium phosphate or sodium phosphate; the reaction in step 3 is performed at a temperature of 70-110° C.; the reaction solvent in step 3 is selected from the group consisting of water or other high-boiling point solvents or a combination thereof, wherein the other high-boiling point solvents are selected from the group consisting of dioxane, DMF, or DMSO.

12. The method according to claim 7, wherein the organic solvent for salifying the K-free base in step 3 is any one selected from the group consisting of methanol, ethanol, isopropanol, dimethylformamide, tetrahydrofuran, methyltetrahydrofuran, dichloromethane, ethyl acetate, and isopropyl acetate or a mixed solvent thereof.

13. The method according to claim 1, preparing the compound M oxazolidinone intermediate, having an enantiomer limit of <0.10% and then using the compound M oxazolidinone intermediate to prepare tedizolid.

14. The method according to claim 1, wherein the compound M oxazolidinone intermediate is prepared according to the following reaction formula:

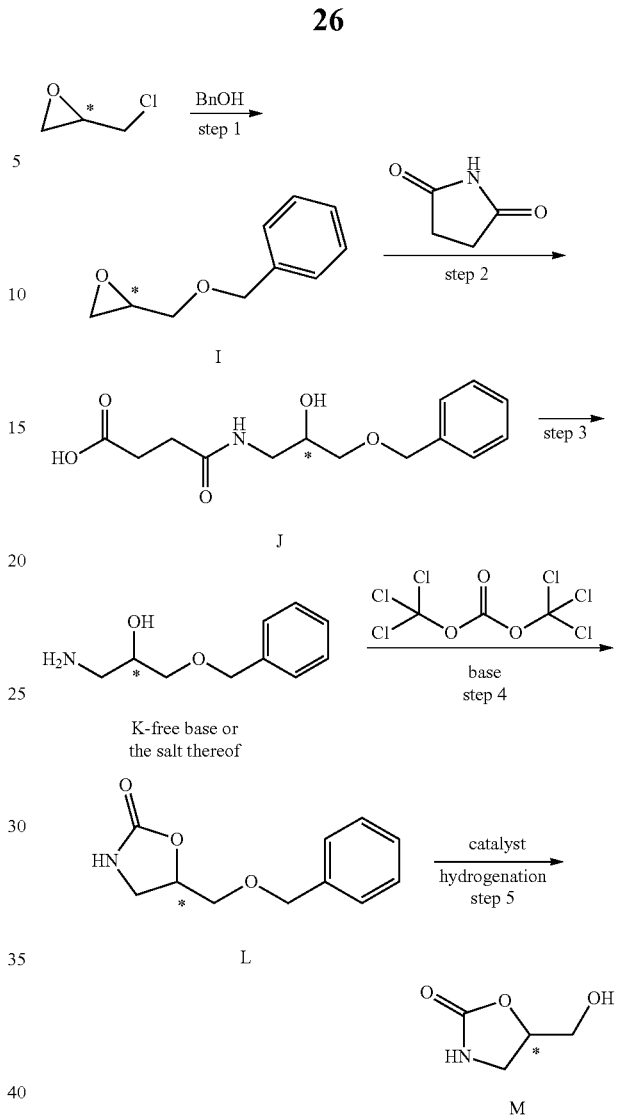

wherein the compound I, compound J, or compound L can be directly subjected to a "one-pot" reaction without being separated, and the compound K salt is selected from the group consisting of the corresponding hydrochloride, sulfate, malate, tartrate, p-toluenesulfonate or lactate; and wherein * stands for the R-enantiomer, the S-enantiomer, or the racemate.

* * * * *